(12) United States Patent
Urban

(10) Patent No.: US 6,936,579 B2
(45) Date of Patent: Aug. 30, 2005

(54) HARD SURFACE CLEANING COMPOSITIONS AND METHOD OF REMOVING STAINS

(75) Inventor: Virginia Lee Urban, New Windsor, NY (US)

(73) Assignee: Reckitt Benckiser Inc., Wayne, NJ (US)

( * ) Notice: Subject to any disclaimer, the term of this patent is extended or adjusted under 35 U.S.C. 154(b) by 217 days.

(21) Appl. No.: 10/210,562

(22) Filed: Jul. 31, 2002

(65) Prior Publication Data

US 2002/0187918 A1 Dec. 12, 2002

Related U.S. Application Data

(63) Continuation of application No. PCT/GB01/00384, filed on Jan. 31, 2001.

(30) Foreign Application Priority Data

Feb. 1, 2000 (GB) .............................................. 0002229

(51) Int. Cl.[7] .............................. C11D 7/50; C11D 7/30
(52) U.S. Cl. ........................ 510/412; 510/273; 510/365
(58) Field of Search ................................. 510/273, 365, 510/412, 238, 506, 477, 434, 424, 505, 422, 362, 417; 252/364; C11D 17/00, 3/37

(56) References Cited

U.S. PATENT DOCUMENTS

| 4,859,359 | A | | 8/1989 | DeMatteo et al. |
|---|---|---|---|---|
| 5,039,441 | A | | 8/1991 | Thomas et al. |
| 6,046,148 | A | * | 4/2000 | Toussaint et al. ........... 510/235 |
| 6,221,823 | B1 | | 4/2001 | Crisanti et al. |

FOREIGN PATENT DOCUMENTS

| GB | 2 306 499 A | 5/1997 |
|---|---|---|
| GB | 2 319 179 A | 5/1998 |
| GB | 2 329 901 A | 4/1999 |
| WO | WO 97/15649 | 5/1977 |
| WO | WO 97/19158 A1 | 5/1997 |
| WO | WO 97/43369 | 11/1997 |
| WO | WO 99/61569 | 12/1999 |

\* cited by examiner

Primary Examiner—Gregory Webb
(74) Attorney, Agent, or Firm—Akin Gump Strauss Hauer & Feld, LLP

(57) ABSTRACT

Improved hard surface cleaning compositions having an acidic pH, providing good removal of soap scum stains, and further feature low levels of irritability to the user. The compositions comprise about 0.1–10% by weight of an acid sequestrant constituent; about 0.1–10% by weight of a mixture of hydrophobic and hydrophilic solvents; about 0.001–1% by weight of a single constituent which exhibits both anionic surfactant and hydrotrope properties; about 0–20% by weight of one or more optional constituents; the balance to 100% by weight of water, wherein the aqueous hard surface cleaning composition exhibits a pH of 7 or less, especially a pH of about 5 or less. Although acidic, the improved hard surface cleaning compositions feature low irritability to the eyes and skin of consumers. The compositions also provide disinfecting effects.

19 Claims, No Drawings

HARD SURFACE CLEANING COMPOSITIONS AND METHOD OF REMOVING STAINS

CROSS-REFERENCE TO RELATED APPLICATIONS

This application is a continuation of International Application No. PCT/GB01/00384, filed Jan. 31, 2001, which was published in the English language on Aug. 9, 2001, under International Publication No. WO 01/57174 A1 and the disclosure of which is incorporated herein by reference.

BACKGROUND OF THE INVENTION

The present invention relates to improved cleaning compositions which find particular use in hard surface cleaning applications.

Cleaning compositions are commercially important products and enjoy a wide field of utility in assisting in the removal of dirt and grime from surfaces, especially those characterized as useful for cleaning "hard surfaces". Hard surfaces include those which are frequently encountered in lavatories, for example lavatory fixtures such as toilets, shower stalls, bathtubs, bidets, sinks, etc., as well as countertops, walls, floors, etc. In such lavatory environments various forms of undesirable residues are known to form including hard water stains as well as "soap scum stains". Hard water stains are mineral stains caused by the deposition of salts, such as calcium or magnesium salts, frequently present in hard water. Soap scum stains are residues of fatty acid soaps, such as soaps which are based on alkaline salts of low fatty acids. These fatty acids are known to precipitate in hard water due to the presence of metal salts therein leaving an undesirable residue upon such surfaces.

Various formulations in compositions of cleaning agents have been produced, and it is generally known to the art which cleaning agents are generally suited for one type of stain but not necessarily for both classes of stains. For example, it is known to the art that highly acidic cleaning agents comprising strong acids, such as hydrochloric acids, are useful in the removal of hard water stains. However, the presence of strong acids is known to be an irritant to the skin and further has the potential of toxicological danger. Other classes of cleaning compositions and formulations are known to be useful upon soap scum stains. However, generally such compositions comprise an organic and/or inorganic acid, one or more synthetic detergents from commonly recognized classes such as those described in U.S. Pat. No. 5,061,393; U.S. Pat. No. 5,008,030; U.S. Pat. No. 4,759,867; U.S. Pat. No. 5,192,460; U.S. Pat. No. 5,039,441. Generally, the compositions described in these patents are claimed to be effective in the removal of soap scum stains from such hard surfaces and may find further limited use in other classes of stains.

However, the formulations of most of the compositions within the aforementioned patents generally have relatively high amounts of acids (organic and/or inorganic), which raises toxicological concerns, and further none of the above patents provides any disinfecting properties.

Compositions are known to the art which do provide disinfection and sanitization through the use of certain classes of anionic surfactants coupled with an acidic component, such as that described in U.S. Pat. No. 5,143,720. However, the compositions in this U.S. patent would not be expected nor are believed to provide any significant cleaning benefit and thus would not be particularly effective in the removal of residues, particularly hard water stains and soap scum stains.

International Patent Publication WO 97/15649 describes a hard surface composition having an acidic pH. The composition provides good removal of soap scum stains, and features low levels of irritability to the user.

BRIEF SUMMARY OF THE INVENTION

Thus, it is among the objects of the invention to provide improved cleaning compositions which provide the benefits of low toxicity, hard water stain removal and soap scum stain removal, are effective in providing a disinfecting effect, and facilitate the removal of soap scum stains and hard water stains, especially from hard surfaces. It is a further object of the invention to provide improved cleaning compositions which are particularly effective in hard water stain removal and soap scum stain removal, and which further features minimal irritability to the eyes, skin or mucous tissues of a consumer.

It is yet a further object of the invention to provide a readily pourable and readily pumpable cleaning composition which features the benefits described above.

It is a further object of the invention to provide a process for the improvement of the simultaneous cleaning and sanitization of hard surfaces, which process comprises the step of: providing a cleaning composition as outlined above, and applying an effective amount to a hard surface requiring such treatment.

These and other objects of the invention shall be more apparent from a reading of the following specification and of the claims.

According to the invention, there is provided an aqueous hard surface cleaning compositions. The compositions include the following:

Constituent (A): an acid sequestrant comprising citric acid together with another organic acid;

Constituent (B): a mixture of hydrophobic and hydrophilic solvents; and

Constituent (C): a material having surfactant and hydrotrope properties.

The compositions of the invention may also include one or more further optional constituents such as known art additives. By way of non-limiting example, such constituents include: further surfactants, particularly surfactants which are useful for the removal of greasy soils, foaming agents and foam stabilizers, coloring agents, including dyes and pigment compositions, fragrances (whether natural or synthetically produced), fragrance adjuvants and/or fragrance solubilizers, viscosity modifying agents including thickeners or gelling agents, pH-adjusting agents, pH buffers, antioxidants, water softening agents, further solubilizing agents which might be useful in the solubilization of one or more of the constituents in water, preservative compositions, as well as other known art additives not particularly elucidated here. Such constituents as described above include known art compositions, including those described in *McCutcheon's Detergents and Emulsifiers*, North American Edition, 1998; Kirk-Othmer Encyclopedia of Chemical Technology, 4th Ed., Vol. 23, pp. 478–541, the contents of which are herein incorporated by reference.

The compositions according to the invention are preferably acidic in character, exhibiting a pH of less than 7. Desirably, the pH is in the range of about 1 to about 5, yet more desirably is a pH in the range of about 1 to about 4, and most desirably is a pH of about 1 to about 3.

In a further aspect of the invention, there is also provided an improved process for cleaning and disinfecting surfaces, especially hard surfaces, which includes the step of applying to the surface an effective amount of a stain releasing and disinfecting composition as taught herein to such surface.

DETAILED DESCRIPTION OF THE INVENTION

Constituent A. The constituents which comprise Constituent A, namely the acid sequestrant according to the invention is a combination of citric acid together with another acid which is found to be effective in the removal of hard water stains from hard surfaces, particularly lavatory surfaces as denoted above.

Exemplary useful acids include: citric acid, cresylic acid, dodecylbenzene sulfonic acid, phosphoric acid, salicylic acid, sorbic acid, sulfamic acid, acetic acid, benzoic acid, boric acid, capric acid, caproic acid, cyanuric acid, dihydroacetic acid, dimethylsulfamic acid, propionic acid, polyacrylic acid, 2-ethyl-hexanoic acid, formic acid, fumaric acid, 1-glutamic acid, isopropyl sulfamic acid, naphthenic acid, oxalic acid, phosphorous acid, valeric acid, benzene sulfonic acid, xylene sulfonic acid, as well as any acid listed as a registered pesticide active ingredient with the United States Environmental Protection Agency. Further useful acids include: sulfonic acids, maleic acid, acetic acid, adipic acid, lactic acid, butyric acid, gluconic acid, malic acid, tartaric acid, as well as glycolic acid. Desirably glycolic acid and citric acid are used, as they are effective, in plentiful supply, and may be advantageously used. These acid sequestrants provide free acidity within the cleaning composition. The free acid reacts with fatty acid metal salts within soap scum stains, releasing the metal ions and freeing the fatty acid, which facilitates the removal of these undesired stains from hard surfaces. These acid sequestrants also sequester the resulting free metal ions which are released from the soap scum stains. Also, where the acid sequestrants are selected to feature disinfecting properties, they concomitantly provide requisite anti-microbial activity necessary to disinfect the cleaned surface.

Constituent A comprises a first acid sequestrant which comprises citric acid and a second acid sequestrant which is at least one further acid described above, as it has been observed by the inventor that citric acid provides good disinfecting action in the compositions of the invention, but in certain formulations may be insufficiently acidic in order to effectively remove certain stains. The addition of at least one further acid provides additional cleaning effect which was not observed in certain formulations with citric acid alone. Preferably, the further acid is selected from the group consisting of lactic acid, tartaric acid, and glycolic acid.

The first and second acid sequestrants of Constituent A are desirably present in the formulations in ranges of about 0.1 to about 10% by weight, preferably about 1 to about 8% by weight, and more preferably about 4 to about 6% by weight, based on the total weight of a composition. In preferred embodiments however, citric acid comprises at least about 0.1% by weight of the total weight of the acids of Constituent A, more preferably citric acid comprises at least about 25% by weight, and most preferably citric acid comprises at least about 50% by weight of the acids of Constituent A.

Constituent B. The constituents of Constituent B are a mixture of hydrophobic and hydrophilic solvents, which act to assist in the dissolution of the fatty acids from a surface being cleaned. Certain fatty acids present in the soap scum residues are solubilized and/or rendered at least partially miscible in water due to the presence of Constituent B, which facilitates the removal of the stain from the surface. The solvents of Constituent B are also useful in penetrating the stain and act as a carrier for the further constituents of the invention, especially the constituents comprising Constituent A, thus bringing them through the layer of the stain to the surface upon which the stain is present, and thereby aiding in the effective dissolution of the stain and its removal.

The hydrophobic solvent constituent of Constituent B should demonstrate solubilization of the aliphatic portions of the fatty acids within the soap scum stains. Exemplary useful hydrophobic solvents include mineral spirits, tripropylene glycol n-butyl ether, propylene glycol phenyl ether, dipropylene glycol n-propyl ether, ethylene glycol phenyl ether, and particularly propylene glycol n-butyl ether and dipropylene glycol n-butyl ether. The hydrophobic solvent may be one such solvent or a mixture of two or more hydrophobic solvents.

The hydrophobic solvent exhibits a solubility in water of about 0 ml/100 ml to about 20 ml/100 ml and preferably comprises about 51 to about 99% of the total weight of Constituent B within the compositions according to the invention. More preferably, the hydrophobic solvent comprises about 60 to about 95%, most preferably about 70 to about 90% of the total weight of Constituent B of the compositions according to the invention. The hydrophilic solvent of Constituent B may be one which is useful in solubilizing or improving the miscibility of the hydrophobic solvent in water. Where the hydrophobic solvent of Constituent B dissolves the soap fatty acids, the hydrophilic solvent acts to solubilize the hydrophobic solvent in water, and thereby provides effective solubility with the aqueous phase and facilitates the removal of the hydrophobic solvent and dissolved soap fatty acids from the surface being cleaned.

By way of non-limiting example, useful hydrophilic solvents include certain alcohols, glycols, acetates, ether acetates and glycol ethers including propylene glycol methyl ether, dipropylene glycol methyl ether, tripropylene glycol methyl ether, propylene glycol n-propyl ether, ethylene glycol n-butyl ether, diethylene glycol n-butyl ether, diethylene glycol methyl ether, propylene glycol, ethylene glycol, isopropanol, ethanol, methanol, diethylene glycol monoethyl ether acetate and particularly useful is ethylene glycol monobutyl ether acetate. A single hydrophilic solvent or two or more hydrophilic solvents may be used.

The hydrophilic solvents comprising Constituent B of this invention should exhibit good solubility in water, preferably approaching or demonstrating "infinite solubility," and preferably comprise about 1 to about 49%, preferably about 1 to about 40%, and still more preferably about 10 to about 30%, based on the total weight of Constituent B within the compositions according to the invention.

With regard to the effective amounts of Constituent B, Constituent B is desirably present in amounts of about 0.1 to about 10% by weight based on the total cleaning composition weight, preferably about 2 to about 8% by weight, and more preferably about 3 to about 6% by weight.

Constituent C. The constituents comprising Constituent C provide for the reduction of the interfacial tension between the soil and the compositions of the invention which facilitates the wetting of the stain as well as providing a hydrotropic functionality. Such a hydrotropic functionality aids in the solubilization of greater amounts of fatty acids in a stain and in the removal of the stain from a surface.

Exemplary materials useful as Constituent C include one or more compounds such as: alkyl phenoxy benzene disulfonates (also known as alkyl diphenyl oxide disulfonates), linear alkyl benzene sulfonates and alkylnaphthalene sulfonates and salts thereof. Such compositions are known to the art, and available as anionic surfactants. These also include but are not limited to: alkali metal salts, ammonium salts, amine salts, aminoalcohol salts or the magnesium salts of one or more of the following compounds: alkyl sulfates, alkyl ether sulfates, alkylamidoether sulfates, alkylaryl polyether sulfates, monoglyceride sulfates, alkylsulfonates, alkylamide sulfonates, alkylarylsulfonates, olefinsulfonates, paraffin sulfonates, alkyl sulfosuccinates, alkyl ether sulfosuccinates, alkylamide sulfosuccinates, alkyl sulfosuccinamate, alkyl sulfoacetates, alkyl phosphates, alkyl ether phosphates, acyl sarcosinates, acyl isethionates, and N-acyl taurates. Generally, the alkyl or acyl radical in these various compounds comprise a carbon chain containing 12 to 20 carbon atoms.

Exemplary alkyl phenoxy benzene disulfonates (also known as alkyl diphenyl oxide disulfonates) include metal salts and organic salts of alkylphenoxy benzene disulfonates, such as sodium dodecyl diphenyloxide disulfonate, sodium hexyl diphenyloxide disulfonate, sodium n-decyl diphenyloxide disulfonate, as well as sodium n-hexadecyl diphenyloxide disulfonate. Other metal counterions or organic counterions may be substituted in the place of the sodium noted in the recited alkyl phenoxy benzene disulfonates noted above, as well as mixtures of two or more alkyl phenoxy benzene disulfonates. Many of these materials are available under the Dowfax® (Dow Chemical, Midland, Mich.) or Calfax® (Pilot Chemical, Santa Fe Springs, Calif.) trademarks.

Exemplary linear alkyl benzene sulfonates include metal salts and organic salts of linear alkyl benzene sulfonates, such as sodium dodecylbenzene sulfonate, sodium nonylbenzene sulfonate, isopropylamine salts of linear alkyl benzene sulfonic acid, triethanolamine dodecylbenzene sulfonate, diethanolamine dodecylbenzene sulfonate, potassium dodecylbenzene sulfonate, sodium tridecylbenzene sulfonate, as well as mixtures of sodium dodecylbenzenesulfonate with sodium toluene sulfonate, sodium cumene sulfonate and/or with sodium xylene sulfonate. Other metal counterions or organic counterions may be substituted in the place of the counterions noted in the recited linear alkyl benzene sulfonates noted above, as well as mixtures of two or more linear alkyl benzene sulfonates.

Exemplary alkylnaphthalene sulfonates include metal salts and organic salts of alkylnaphthalene sulfonates such as sodium diisopropylnaphthalene sulfonate, butylnaphthalene sodium sulfonate, nonylnaphthalene sodium sulfonate, sodium dibutylnaphthalene sulfonate and sodium dimethylnaphthalene sulfonate. Other metal counterions or organic counterions may be substituted in the place of the counterions noted in the recited alkylnaphthalene sulfonates noted above, as well as mixtures of two or more alkylnaphthalene sulfonates.

Further useful as constituents used in Constituent C include sodium xylene sulfonate, sodium cumene sulfonate, and naphthalene sulfonates.

Constituent C is a single constituent which exhibits both anionic surfactant and hydrotrope properties. With regard to the effective amounts of Constituent C, Constituent C is present in amounts of about 0.001 to about 1% by weight based on the total cleaning composition weight.

As is noted above, the compositions according to the invention are aqueous in nature. Water is added to Constituents A, B and C in order to provide 100% by weight of the composition.

The water may be tap water, but is preferably distilled and is most preferably deionized water. If the water is tap water, it is preferably substantially free of any undesirable impurities such as organics or inorganics, especially minerals salts which are present in hard water, which may thus interfere with the operation of Constituents A, B, C, as well as any other optional components of the aqueous The compositions according to the invention may comprise one or more of the following optional components, the total weight of such optional constituents preferably not exceeding about 20% by weight of the total weight of the composition, more preferably not exceeding about 10% by weight, and most preferably less than 10% by weight based on the total weight of the composition according to the invention.

Non-ionic surfactants of the conventionally known and used variety in this class of cleaning agents may be added in effective amounts, i.e., amounts which are shown to be effective in the cleaning compositions in facilitating the removal of greasy soils. Such greasy soils are to be differentiated from the hard water stains and the soap scum stains described earlier in this specification. However, it is also to be appreciated that the non-ionic surfactants of this optional constituent also may be at least partially effective in the solubilization and removal of soap scum stains. Exemplary nonionic surfactants include known nonionic surfactants which generally consist of a hydrophobic moiety, such as $C_6$–$C_{20}$ primary or secondary, branched or straight chain monoalcohols, $C_8$–$C_{18}$ mono- or dialkyphenols, $C_6$–$C_{20}$ fatty acid amides, and a hydrophilic moiety which consists of alkylene oxide units. These nonionic surfactants are, for instance, alkoxylation products of the above hydrophobic moieties, containing from 2 to 30 moles of alkylene oxide. As alkylene oxides, ethylene-, propylene- and butylene oxides and mixtures thereof are used.

Typical examples of such nonionic surfactants are $C_9$–$C_{11}$ primary, straight-chain alcohols condensed with 5–9 moles of ethylene oxide, $C_{12}$–$C_{15}$ primary straight chain alcohols condensed with from 6–12 moles of ethylene oxide, or with 7–9 moles of a mixture of ethylene oxide and propylene oxide, $C_{11}$–$C_{15}$ secondary alcohols condensed with from 3–15 moles of ethylene oxide, and $C_{10}$–$C_{18}$ fatty acid diethanolamides, and tertiary amine oxides such as higher alkyl di(lower alkyl or lower substituted alkyl)amine oxides. Other useful nonionic surfactants include certain alkoxylated linear aliphatic alcohol surfactants which are believed to be the condensation products of a $C_8$–$C_{10}$ hydrophilic moiety with alkylene oxides, especially polyethylene oxide and or polypropylene oxide moieties. Such alkoxylated linear alcohol surfactants are presently commercially available under the trademark PolyTergent® (BASF, Mont. Olive, N.J.). Such nonionic surfactants are known to the art, and are more particularly described in *McCutcheon's Detergents and Emulsifiers*, noted above.

Foaming agents, and foam stabilizing agents may be provided, including alkyl sulfates, alkyl sulfonates, amine oxides, as well as alkanolamides. Such may be especially desirable where the composition is packaged in a pressurized device, i.e., an aerosol canister or in a hand-held pumpable container (such as a hand held trigger-spraying vessel).

Further optional, but desirable constituents, include fragrances, natural or synthetically produced. Such fragrances may be added in any conventional manner, admixing to a composition or blending with other constituents used to form a composition, in amounts which are found to be useful to enhance or impart the desired scent characteristic to the composition, and/or to cleaning compositions formed therefrom.

In compositions which include a fragrance, it is frequently desirable to include a fragrance solubilizer which assists in the dispersion, solution or mixing of the fragrance constituent in an aqueous base. These include known art compounds, including condensates of 2 to 30 moles of ethylene oxide with sorbitan mono- and tri-$C_{10}$–$C_{20}$ alkanoic acid esters having a HLB of 8 to 17 are also known as nonionic surfactants. Further examples of such suitable surfactants include water soluble nonionic surfactants of which many are commercially known and, by way of non-limiting example, include the primary aliphatic alcohol ethoxylates, secondary aliphatic alcohol ethoxylates, alkylphenol ethoxylates and ethylene-oxide-propylene oxide condensates of primary alkanols, and condensates of ethylene oxide with sorbitan fatty acid esters. This fragrance solubilizer component is added in minor amounts, preferably in an amount effective in aiding in the solubilization of the fragrance component, but not in any significantly greater proportion, such that it would be considered as a detergent constituent. Such minor amounts recited herein are generally up to about 0.5% by weight of the total composition, but more generally present an amount of about 0.1% by weight and less, and preferably present in amounts of about 0.05% by weight and less.

Further optional, but advantageously included constituents are one or more coloring agents which find use in modifying the appearance of the compositions and enhance their appearance from the perspective of a consumer or other end user. Known coloring agents may be incorporated in the compositions in any effective amount to improve or impart to compositions a desired appearance or color. Such a coloring agent or coloring agents may be added in a conventional fashion, i.e., admixing to a composition or blending with other constituents used to form a composition.

The use of one or more pH-adjusting agents, including minor amounts of mineral acids, basic compositions, and organic acids may be used. An exemplary composition includes citric acid, such as is available in an anhydrous salt form of an alkali metal citric acid. The addition of an effective amount of such a pH-adjusting agent is useful in establishing a targeted pH range for compositions according to the invention. The addition of an effective amount of a pH buffering composition so as to maintain the pH of the inventive compositions may also be added. While the composition of the invention generally does not require a pH buffering composition, the use of such a pH buffering composition may provide the benefit of hard water ion sequestration. Examples of such useful pH buffer compounds and/or pH buffering systems or compositions are alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, citrates, and their alkali metal salts. Such buffers keep the pH ranges of the compositions of the present invention within acceptable limits. Others, not particularly elucidated here may also be used. Preferably, citric acid, such as is available in an anhydrous salt form of an alkali metal citric acid is added as it is readily commercially available, and effective. The addition of such a buffering agent is desirable in certain cases wherein long term, i.e., prolonged storage, is to be anticipated for a composition, as well as insuring the safe handling of said aqueous composition.

Preservatives which do not include a disinfectant component may also be added in minor amounts in the formulations according to the invention. Compositions known in the art may be used. Examples of such preservatives compounds include those which are presently commercially available under the trademarks Kathon® CG/ICP (Rohm & Haas, Philadelphia Pa.), Suttocide® A (Sutton Labs, Chatham N.J.) as well as Midtect® TFP (Tri-K Co., Emerson, N.J.). Such preservatives are generally added in only minor amounts, i.e., amounts of about 0.5% by weight of the total composition, more generally an amount of about 0.1% by weight and less, and preferably present in amounts of about 0.05% by weight and less.

Thickening and/or gelling agents may be added to the hard surface cleaning compositions according to the present invention in order to modify the viscous and/or thixatropic properties thereof. For example, in certain applications it is contemplated that it may be desirable to provide a more viscous, viz., higher viscosity than that of water, whether for aesthetic or functional reasons.

For example, the addition of a suitable amount of a gelling agent may be desired not only for aesthetic reasons but also to limit the spreading of the composition as it is applied to a surface. This function is desirable in providing a means to apply the composition over a limited area, such as directly onto a stain, without applying an excess onto the surrounding area of a surface. This function also aids in the surface retention time on non-horizontal surfaces, ensuring that the cleaning composition is in contact with a stained surface without flowing off too rapidly. Similarly, thixotropic properties may also be desired under certain circumstances. In order to provide such functional features to the composition, known thickening and gelling agents including, but not limited to, cellulose compounds, xanthan gums, polymers and/or clays may be added. For xanthan gums, those available under the Kelco or Keltrol trademarks are useful.

The benefits of the compositions described in this specification include particularly: disinfection, good removal of hard water stains, good removal of soap scum stains, relatively low toxicity, as well as ease in handling of the composition due to its readily pourable or pumpable characteristic. Further, when one or more of the optional constituents are added, i.e., fragrance, foaming agents, coloring agents, the aesthetic and consumer appeal of the product is favorably improved.

Notwithstanding that the pH of preferred embodiments of compositions according to the present invention is less than about 3, it has surprisingly been found that these formulations do not appear to be particularly irritating to the eyes, skin or mucous tissues of a consumer. Such is a surprising effect, as the presence of the acids in the formulation which are beneficial in the removal of hard water stains, as well as the relatively low pH of the formulation would be expected to be a severe irritant to the eyes, skin or mucous tissues of a consumer.

The compositions according to the invention are useful in the cleaning and/or disinfecting of hard surfaces, having deposited soil thereon. In such a process, cleaning and disinfecting of such surfaces comprises the step of applying a stain releasing and disinfecting effective amount of a composition as taught herein to such a stained surface. Afterwards, the compositions are optionally but desirably wiped, scrubbed or otherwise physically contacted with the hard surface, and further optionally, may be subsequently rinsed from such a cleaned and disinfected hard surface.

The hard surface cleaner composition provided according to the invention can be desirably provided as a ready to use product in a manually operated spray-dispensing container. Such a typical container is generally made of synthetic polymer plastic material, such as polyethylene, polypropylene, polyvinyl chloride or the like, and includes a spray nozzle, a dip tube and associated pump dispensing parts, and is thus ideally suited for use in a consumer "spray and wipe" application. In such an application, the consumer generally applies an effective amount of the cleaning composition using the pump and within a few moments thereafter, wipes off the treated area with a rag, towel, or sponge, usually a disposable paper towel or sponge. In certain applications, however, especially where undesirable stain deposits are heavy, the cleaning composition according to the invention may be left on the stained area until it has effectively loosened the stain deposits, after which it may then be wiped off, rinsed off, or otherwise removed. For particularly heavy deposits of such undesired stains, multiple applications may also be used.

In a yet a further embodiment, the compositions according to the invention may be formulated so that they may be useful in conjunction with an "aerosol" type product wherein they are discharged from a pressurized aerosol container. If the inventive compositions are used in an aerosol type product, it is preferred that corrosion resistant aerosol containers, such as coated or lined aerosol containers be used. Such are preferred as they are known to be resistant to the effects of acidic formulations. Known art propellants, such as liquid propellants as well as propellants of the non-liquid form, i.e., pressurized gases, including carbon dioxide, air, nitrogen, hydrocarbons as well as others may be used.

Whereas the present invention is intended to be used in the types of liquid forms described, nothing in this specification shall be understood as to limit the use of the composition according to the invention with a further amount of water to form a cleaning solution therefrom. In such a proposed diluted cleaning solution, the greater the proportion of water added to form said cleaning solution, the greater may be the reduction of the rate and/or efficacy of the thus formed cleaning solution in the cleaning of a hard surface, as well as a reduction in disinfectant efficacy.

Accordingly, longer residence times upon the stain to effect their loosening and/or the usage of greater amounts may be necessitated. Conversely, nothing in the specification shall be also understood to limit the forming of a "super-concentrated" cleaning composition based upon the composition described above. Such a super-concentrated composition is essentially the same as the compositions described above except in that they include a lesser amount of water.

While the cleaning compositions are most beneficial for use in their form, i.e., their form as described above, they may also be diluted to form a cleaning composition therefrom. Such cleaning compositions may be easily prepared by diluting measured amounts of the compositions in further amounts of water by the consumer or other end user in certain weight ratios of composition to water, and optionally, agitating the same to ensure even distribution of the composition in the water. The aqueous compositions according to the invention may be used without further dilution, but may also be used with a further aqueous dilution, i.e., in composition to water concentrations of about 1:0 to extremely dilute dilutions such as about 1:10,000. but preferably would be used in a weight or volume ratio proportion of about 1:10 to about 1:100. Generally better results and faster removal are to be expected at lower relative dilutions of the composition and the water.

The following examples below illustrate exemplary formulations and preferred formulations of the composition according to the instant invention. It is to be understood that these examples are presented by means of illustration only and that further useful formulations falling within the scope of this invention and the claims may be readily produced by one skilled in the art and not deviate from the scope and spirit of the invention. Throughout this specification and in the accompanying claims, weight percents of any constituent are to be understood as the weight percent of the active portion of the referenced constituent, unless otherwise indicated.

EXAMPLE FORMULATIONS

Preparation of Example Formulations

Exemplary formulations illustrating certain preferred embodiments of the inventive compositions and described in more detail in Table I below were formulated generally in accordance with the following protocol.

Into a suitably sized vessel, a measured amount of water was provided after which the constituents were added in the following sequence: thickening agent, surfactants, solvents, acid and lastly the coloring and fragrance constituents. Mixing, which generally lasted from 5 minutes to 120 minutes was maintained until the particular formulation appeared to be homogeneous. The exemplary compositions were readily pourable, and retained well mixed characteristics (i.e., stable mixtures) upon standing for extended periods, even in excess of 120 days. It is to be noted that the constituents might be added in any order, but it is preferred that water be the initial constituent provided to a mixing vessel or apparatus, as it is the major constituent and addition of the further constituents thereto is convenient. In another preferred method, a premix of solvent and gelling agent is made, which is then added to water and the remaining constituents.

Examples of inventive formulations are shown in Table 1 below.

TABLE 1

| Constituent | Ex. 1 (wt. %) | Ex. 2 (wt. %) |
| --- | --- | --- |
| PolyTergent ® SL-62 | 0.9000 | 0.9000 |
| Stepanol ® WAC | 2.1000 | 2.1000 |
| Dowfax ® 3B2 | 2.1000 | 2.1000 |
| Dowanol ® DPnB | 2.7300 | 2.7300 |
| Dowanol ® PnP | 0.8900 | 0.8900 |
| Citric acid anhydrous | 2.5000 | 2.5000 |
| Glycolic acid | 2.8000 | 2.8000 |
| Keltrol ® T | 0.6000 | — |
| Fragrance | 0.3000 | 0.3000 |
| Dyes | 0.0012 | 0.0012 |
| Deionized water | q.s. | q.s. |

The individual constituents which were used to produce the formulations according to Table 1 are described in more detail in Table 2 below.

TABLE 2

| Constituent | |
| --- | --- |
| PolyTergent ® SL-62 | described to be a nonionic alkoxylated linear alcohol surfactant, approx. 8 moles oxyethylene per molecule (BASF, Mt. Olive, NJ) |
| Stepanol ® WAC | sodium lauryl sulfate (29% actives) (Stepan Company, Northfield, IL) |
| Dowfax ® 3B2 | sodium n-decyl diphenyloxide disulfonate (45% actives) as an anionic surfactant/hydrotrope (Dow Chemical Co., Midland MI) |

TABLE 2-continued

| Constituent | |
|---|---|
| Dowanol ® DPnB | dipropylene glycol n-propyl ether as hydrophobic solvent, (Dow Chemical Co., Midland MI) |
| Dowanol ® PnP | propylene glycol n-propyl ether as hydrophilic solvent (Dow Chemical Co., Midland MI) |
| Citric acid | citric acid, anhydrous USP grade as acid sequestrant |
| Glycolic acid | hydroxyacetic acid as acid sequestrant (70% actives) (DuPont Specialty Chemicals, Wilmington DE) |
| Dyes | proprietary dyes |
| Fragrance | proprietary fragrance |
| Keltrol ® T | xanthan gum (Kelco Co., San Diego, CA) |
| Deionized water | deionized water |

Cleaning Efficacy

Formulations of the present invention are expected to have good cleaning efficacy.

Evaluation of Ocular Irritation

The ocular irritation characteristics of formulations according to the invention are expected to have good performance using the known Draize Eye test protocol such that the formulations would be classified under Category III for primary dermal irritation under the guidelines of the USA Environmental Protection Agency.

Evaluation of Antimicrobial Efficacy

The formulation of Example Ex. 2 has acceptable antimicrobial efficacy against one or more organisms such as *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (ATCC 15442). Using an AOAC Germicidal Spray test, Ex. 2 was found to have zero positive tubes out of ten tubes tested (0/10) when subjected to a ten minute contact time with the aforementioned organisms at room temperature (~22° C.). The formulations of the present invention should have efficacy against other commonly found bacteria and viruses which are found on hard surfaces.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An aqueous hard surface cleaning and disinfecting composition comprising:
    (a) a first acid sequestrant constituent comprising citric acid and at least one second acid sequestrant selected from the group consisting of cresylic acid, dodecylbenzene sulfonic acid, phosphoric acid, salicylic acid, sorbic acid, sulfamic acid, acetic acid, benzoic acid, boric acid, capric acid, caproic acid, cyanuric acid, dihydroacetic acid, dimethylsulfamic acid, propionic acid, polyacrylic acid, 2-ethyl hexanoic acid, formic acid, fumaric acid, 1-glutamic acid, isopropyl sulfamic acid, naphthenic acid, oxalic acid, phosphorus acid, valeric acid, benzene sulfonic acid, xylene sulfonic acid, sulfonic acids, maleic acid, acetic acid, adipic acid, lactic acid, butyric acid, gluconic acid, malic acid, tartaric acid, and glycolic acid;
    (b) a mixture of hydrophobic and hydrophilic solvents wherein said hydrophobic solvent exhibits a solubility in water of about 0 to about 20 ml per 100 ml of water, and which comprises about 51 to about 99 wt. % of said mixture of solvents, and wherein said hydrophilic solvent comprises about 1 to about 49 wt % of said mixture of solvents;
    (c) about 0.001 to less than about 1% by weight of a single constituent which exhibits both anionic surfactant and hydrotrope properties and is at least one selected from the group, consisting of alkyl phenoxy benzene disulfonates, linear alkyl benzene sulfonates, alkyl naphthalene sulfonates and salts thereof;
    (d) about 0 to about 20% by weight of one or more optional constituents; and
    (e) the balance to 100% by weight water, wherein the aqueous hard surface cleaning and disinfecting composition exhibits a pH of 7 or less.

2. The aqueous hard surface cleaning and disinfecting composition according to claim 1 wherein the second acid sequestrant is selected from the group consisting of lactic acid, tartaric acid, and glycolic acid.

3. The aqueous hard surface cleaning and disinfecting composition according to claim 1 wherein the acid sequestrant constituent comprises at least about 25% by weight of citric acid.

4. The aqueous hard surface cleaning and disinfecting composition according to claim 1 wherein the total acid sequestrant constituent is present in an amount of about 0.1 to about 10% by weight.

5. The aqueous hard surface cleaning and disinfecting composition according to claim 1 wherein the mixture of hydrophobic and hydrophilic solvents comprises a hydrophobic solvent which is an organic solvent which demonstrates solubilization of an aliphatic portion of a fatty acid within a soap scum stain.

6. The aqueous hard surface cleaning and disinfecting composition according to claim 1 wherein the mixture of hydrophobic and hydrophilic solvents comprises a hydrophobic solvent which is an organic solvent selected from the group consisting of mineral spirits, tripropylene glycol n-butyl ether, propylene glycol phenyl ether, dipropylene glycol n-propyl ether, and ethylene glycol phenyl ether.

7. The aqueous hard surface cleaning and disinfecting composition according to claim 1 wherein the mixture of hydrophobic and hydrophilic solvents comprises a hydrophilic solvent which is an organic solvent effective in solubilizing the hydrophobic solvent in water.

8. The aqueous hard surface cleaning and disinfecting composition according to claim 7 wherein the mixture of hydrophobic and hydrophilic solvents comprises a hydrophilic solvent selected from the group consisting of glycol methyl ether, dipropylene glycol methyl ether, tripropylene glycol methyl ether, propylene glycol n-propyl ether, ethylene glycol n-butyl ether, diethylene glycol n-butyl ether, diethylene glycol methyl ether, propylene glycol, ethylene glycol, isopropanol, ethanol, methanol, and diethylene glycol monoethyl ether.

9. The aqueous hard surface cleaning and disinfecting composition according to claim 1 wherein the mixture of hydrophobic and hydrophilic solvents is present in an amount of about 2 to about 8% by weight.

10. The aqueous hard surface cleaning and disinfecting composition according to claim 9 wherein the mixture of hydrophobic and hydrophilic solvents is present in an amount of about 3 to about 6% by weight.

11. The aqueous hard surface cleaning and disinfecting composition according to claim 1 wherein the single constituent which exhibits both anionic surfactant and hydrotrope properties is an alkyl phenoxy benzene disulfonate.

12. The aqueous hard surface cleaning and disinfecting composition according to claim 11 wherein the alkyl phenoxy benzene disulfonate is selected from the group consisting of sodium dodecyl diphenyloxide disulfonate, sodium hexyl diphenyloxide disulfonate, sodium n-decyl diphenyloxide disulfonate, and sodium n-hexadecyl diphenyloxide disulfonate.

13. The aqueous hard surface cleaning and disinfecting composition according to claim 1 further comprising an optional constituent selected from the group consisting of nonionic surfactants, foaming agents, foam stabilizers, coloring agents, fragrances (whether natural or synthetically produced), fragrance adjuvants and/or fragrance solubilizers, viscosity modifying agents, thickeners, gelling agents, pH adjusting agents, pH buffers, antioxidants, water softening agents, further solubilizing agents useful in the solubilization of one or more of the constituents in water, and preservative compositions.

14. The aqueous hard surface cleaning and disinfecting composition according to claim 1 wherein the pH of the composition is from about 1 to about 5.

15. The aqueous hard surface cleaning and disinfecting composition according to claim 1 wherein the pH of the composition is from about 1 to about 4.

16. The aqueous hard surface cleaning and disinfecting composition according to claim 15 wherein the pH of the composition is from about 1 to about 3.

17. The aqueous hard surface cleaning and disinfecting composition according to claim 1 further comprising a gelling agent.

18. The aqueous hard surface cleaning and disinfecting composition according to claim 17 wherein the gelling agent is xanthan gum.

19. A process for the removal of stains from hard surfaces comprising the step of applying an effective amount of the composition according to claim 1 to a hard surface needing such treatment.

* * * * *